United States Patent [19]

Maier

[11] 4,148,624
[45] Apr. 10, 1979

[54] GLYCYLMETHYLPHOSPHINIC ACIDS AND DERIVATIVES AS PLANT GROWTH REGULANTS

[75] Inventor: Ludwig Maier, Arlesheim, Switzerland

[73] Assignee: Ciba-Geigy Corporation, Ardsley, N.Y.

[21] Appl. No.: 891,578

[22] Filed: Mar. 30, 1978

[30] Foreign Application Priority Data

Apr. 1, 1977 [CH] Switzerland ............... 4123/77

[51] Int. Cl.$^2$ ............... A01N 9/36; C07F 9/30
[52] U.S. Cl. ............... 71/86; 260/501.12; 260/502.5; 260/942; 560/171
[58] Field of Search ............... 260/502.5, 501.12, 942; 71/86; 560/171

[56] References Cited

U.S. PATENT DOCUMENTS

| | | | |
|---|---|---|---|
| 3,160,632 | 12/1964 | Toy et al. | 260/502.5 |
| 3,359,266 | 12/1967 | Maier | 260/502.5 |
| 3,455,675 | 7/1969 | Irani | 71/86 |
| 3,850,608 | 11/1974 | Hamm | 71/86 |
| 3,894,861 | 7/1975 | Hartman | 71/76 |
| 4,062,669 | 12/1977 | Franz | 71/86 |

FOREIGN PATENT DOCUMENTS 475287 8/1969 Switzerland ............... 260/502.5

OTHER PUBLICATIONS

Il'ina et al., "Izv. Akad. Nauk, SSSR" 1968, vol. 8, pp. 1860–1862 (English Translation pagination 1759–1761).
Ivanov et al., "J. Gen. Chem. (USSR)", 37 1768–1773 (1966), English Translation, (original pagination 1856–1862).

*Primary Examiner*—Joseph E. Evans
*Attorney, Agent, or Firm*—Harry Falber

[57] ABSTRACT

The invention is concerned with a new process for preparing bis(carboxyalkylamino) phosphinic acids and derivatives thereof, and especially deals with the novel compound bis(glycylmethyl) phosphinic acid of the formula

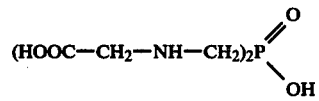

and derivatives thereof including those substituted on the NH-group. This acid, salts and derivatives thereof have plant-growth regulating and herbicidal properties.

6 Claims, No Drawings

GLYCYLMETHYLPHOSPHINIC ACIDS AND DERIVATIVES AS PLANT GROWTH REGULANTS

The present invention relates to a novel process for the production of a new class of phosphinic acids and derivatives thereof, namely the production of bis(carboxyalkylaminomethyl) phosphinic acids of the general formula I

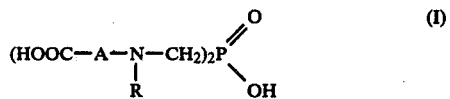

wherein A represents a straight-chain or branched, unsubstituted or substituted alkenyl radical, or together with R represents the hydrocarbon members of a saturated ring, and R furthermore represents a $C_1$–$C_6$ alkyl radical, benzyl, diphenylmethyl or triphenylmethyl.

These novel compounds are interesting intermediates for syntheses in peptide chemistry, but also possess—as do also their derivatives—plant growth-regulating and herbicidal properties.

Attempts to prepare bis(N-glycylmethyl) phosphinic acid by reaction of bis(chlormethylphosphinic acid) with glycine in the presence of NaOH were unsuccessful and yielded other products than the desired bis(glycylmethyl) phosphinic acid [Azv. Akad. Nauk. SSSR, 1969, 623 (English edition)].

It is known form the literature that hypophosphorous acid with formaldehyde and piperidine (unsubstituted secondary amine) in a solution of strong hydrochloric acid yields the hydrochloride of bis(piperidinomethyl) phosphinic acid [Helv. Chim. Acta 50, 1742 (1967) and German patent specifications 1,620,044 and 1,695,449].

It has now been found that, on maintaining certain reaction conditions, it is possible to apply the reaction with formaldehyde and hypophosphorous acid also to functionally substituted secondary amines, namely N-monosubstituted aminoacids.

Such a reaction of hypophosphorous acid with formaldehyde and N-monosubstituted aminoacids is not known from the literature and must be regarded as a novel, inventive process.

The novel process for the production of bis(carboxyalkylaminomethyl)-phosphinic acids of the general formula I comprises reacting 2 moles of a N-monosubstituted or cyclic aminoacid of the formula II

wherein A and R are defined in formula I, with 1 mole of hypophosphorous acid ($H_3PO_2$) and at least 4 moles of formaldehyde in an acid aqueous medium having a pH value below 5 and at a temperature of at least 50° C. Instead of the theoretically necessary 2 moles of formaldehyde, it is necessary to use at least double the excess, preferably up to four times the theoretical amount, of formaldehyde.

The free acid I or the acid addition salt of the strong acid required for the reaction, for example hydrochloric acid, sulphuric acid or phosphoric acid, is formed.

Starting materials of the formula II are in particular N-monoalkylated aminoacids which can be additionally substituted in the radical A by hydroxyl, phenyl, and other radicals occurring in known aminoacids.

Examples of such starting aminoacids of the formula II having a secondary amino group are proline, oxyproline and the following open chain aminoacids, the amino group of which is monosubstituted, for example benzylated: glycine, alanine, valine, leucine, isoleucine, phenylalanine, tyrosine, serine, threonine, glutamic acid, aspartuc acid, β-alanine, γ-aminobutyric acid etc.

In particular, the present incention relates to a process for the production of bis(glycylmethyl) phosphonic acid, the salts, esters, amides and N-substituted derivatives thereof, the new acid and its derivatives themselves, as well as to the use of the new acid and the derivatives thereof as active ingredients of herbicidal and plant growth-regulating compositions.

This new acid and the derivatives thereof have the general formula Ia

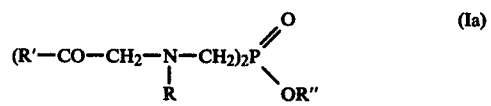

wherein
R represents hydrogen or a $C_1$–$C_6$ alkyl radical, and also benzyl, diphenylmethyl or triphenylmethyl,
R′ represents a group —OH or —$OR_1$, wherein $R_1$ represents a cation, a substituted or unsubstituted $C_1$–$C_6$ alkyl radical, a cycloalkyl radical or a group

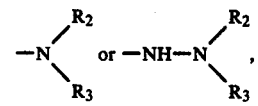

in which each of $R_2$ and $R_3$ independently represents hydrogen, lower alkyl or cyanoalkyl, $R_3$ additionally represents phenyl which is unsubstituted or substituted by halogen, lower alkyl or nitro, and
R″ represents hydrogen or a cation, alkyl, alkenyl, aryl or aralkyl.

If R′ is the —OH group and/or R″ is hydrogen, i.e. the compounds of the formula Ia possess at least one free acid group, then such acids are able to form salts, namely both with the carboxylic acid and the phosphinic acid group. Possible salts are the ammonium and metal salts of alkali metals and alkaline earth metals (Li, Na, K, Ca, Mg), and also of other metals, such as Fe, and salts of amines, such as alkylamines and alkenylamines, or of quaternary ammonio bases. Examples of amines are: methylamine, isopropylamine, tert-butylamine, allylamine. Esters are those compounds where $R_1$ is a cycloalkyl radical or an unsubstituted or substituted alkyl radical.

Possible substituents of alkyl radicals $R_1$ are halogen atoms, hydroxyl and alkoxy groups, hydroxy-(polyalkoxy), carboxyl or cyano groups etc.

Accordingly, $R_1$ can be for example methyl, ethyl, isopropyl, —$CH_2$—$CH_2OH$, —$CH_2$—$CH_2$—$OCH_3$, —$CH_2CF_3$, —$CH_2$—$CH_2Cl$, —$(CH_2)_n$—$COOH$, —$(CH_2)_n$—$(OCH_2)_m$—$OH$, —$(CH_2)_n$—$(OCH_2)_m$—O—Alkyl, wherein n and m are integers from 1 to 3.

The novel process for the production of bis(glycylmethyl) phosphinic acid and its derivatives of the formula Ia comprises reacting a N-substituted glycine of the formula IIa

HOOC—CH₂—NH—R'''  (IIa)

wherein R''' represents a C₁–C₆ alkyl radical or a mono- to triphenylated methyl radical, with hypophosphorous acid (H₃PO₂) and at least twice the excess amount of formaldehyde in an acid aqueous medium having a pH value below 5 and at a temperature of at least 50° C., and, if desired, converting the resulting bis(glycylmethyl) phosphinic acid derivative of the formula Ib

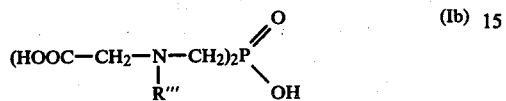

(HOOC—CH₂—N—CH₂)₂P(=O)(OH)  (Ib)
              |
              R''' by removal of a removable group R''' and/or further subsequent operations, into a salt or another derivative of the formula Ia.

The above reaction must be carried out in a strongly acid medium at a pH of below 5, especially at pH 2 to 3 and below, and at elevated temperature between 50° and about 120° C. It is also advantageous to carry out the reaction with the exclusion of oxygen in order to avoid oxidation reactions, and to employ a substantial excess of formaldehyde (up to 4 times the theoretical amount). Suitable solvents are dilute aqueous hydrochloric acid, sulphuric acid or phosphoric acid, optionally in admixture with organic water-miscible solvents.

The reaction proceeds in accordance with the following equation:

2 HOOC—CH₂—NH—R''' + 2CH₂O + H₃PO₂ $\xrightarrow{H^{\oplus}}$

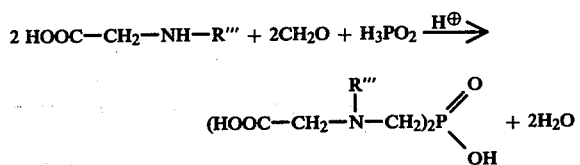

(HOOC—CH₂—N—CH₂)₂P(=O)(OH) + 2H₂O
              |
              R''' affording the acid addition salt (for example the hydrochloride).

If it is desired to prepare an end product in which R is hydrogen, then the radical R''' in the starting material of the formula IIa must be removable after the reaction.

Possible removal radicals R''' are tertiary C₄–C₆ alkyl radicals, especially tert-butyl and aromatically substituted methyl groups, such as benzyl, diphenylmethyl and triphenylmethyl.

If R''' is an aromatically substituted methyl radical (e.g. benzyl), such a radical can be removed by catalytic hydrogenation (e.g. catalytic debenzylation,) by treating the above obtained acid or an acid addition salt thereof in a solvent, such as water, glacial acetic acid, aqueous acetic acid or water+ethanol, catalytically with hydrogen.

A suitable catalyst is 5% palladium on carbon; but it is also possible to use platinum oxide or platinum/carbon. The hydrogenation is carried out under normal pressure and at temperatures between 10° and 50° C., preferably between 20° and 35° C., and takes from ½ hour to 10 hours.

The resulting bis(glycylmethyl) phosphinic acid

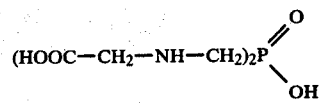

(HOOC—CH₂—NH—CH₂)₂P(=O)(OH)

is a white crystalline solid.

If the removable radical R''' is a tertiary alkyl radical, especially tert-butyl, or benzyl or the diphenylmethyl or triphenylmethyl radical, then this radical can be removed by treating the resulting acid

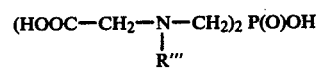

(HOOC—CH₂—N—CH₂)₂ P(O)OH
              |
              R''' or a salt thereof (e.g. the hydrochloride) at 50°–170° C. with HBr (in water or glacial acetic acid), optionally under pressure for 1 to 10 hours.

The conversion of the bis(glycylmethyl)phosphinic acids

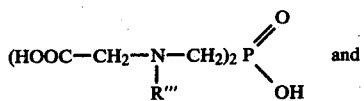

(HOOC—CH₂—N—CH₂)₂ P(=O)(OH)   and
              |
              R'''

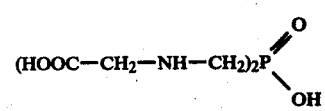

(HOOC—CH₂—NH—CH₂)₂P(=O)(OH)

into corresponding salts, esters, amides and hydrazides is effected by the known methods for such reactions.

The following Examples describe the production of bis(glycylmethyl) phosphinic acid an a number of derivatives of the formula Ia.

EXAMPLE a. With stirring, a mixture of 38.3 g (0.18 mole) of N-benzylglycinehydrochloride (C₆H₅—CH₂—NH—CH₂—COOH.HCl), 12.54 g (0.095 mole) of 50% H₃PO₂ solution in water and 200 ml (2 moles) of conc. HCl is stirred to reflux until a clear solution forms. Then 60.63 g (0.76 mole) of a 38% aqueous formaldehyde solution (four-fold excess) are added dropwise and the reaction mixture is heated to reflux for a further 2 hours. After the reaction mixture has stood for 14 hours at 20° C., the crystallized product is collected by filtration, washed with two 50 ml portions of water and dried. To remove small amounts of benzylglycine hydrochloride (starting material), the product is boiled in 250 ml of ethanol and filtered hot. After drying, 29.5 g (67.9%) of pure white hydrochloride of bis(N-benzylglycylmethyl) phosphinic acid of the formula

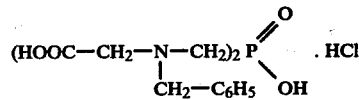

(HOOC—CH₂—N—CH₂)₂ P(=O)(OH) . HCl
              |
              CH₂—C₆H₅ is obtained as residue. Melting point: 211°–214° C. (with decomp.). This acid is soluble in water, water/ethanol and water/methanol, and is insoluble in abs. ethanol and dimethyl sulphoxide.

Analysis:

C₂₀H₂₅N₂O₆P . HCl calculated: C 52,12 H 5,78 N 6,08 Cl 7,70 P 6,73%
found: C 52,0 H 5,8 N 6,2 Cl 7,8 P 6,7%
³¹P(in D₂O)=—15,03 ppm The acid can be titrated with tetramethylammonium hydroxide as tribasic acid.

Infra-red spectrum (in KBr): bands at 2.9μ (OH), 2.35μ (C₆H₅) and 8.5μ (P=O).

b. Debenzylation 1 g of 5% palladium on carbon (catalyst) is added to 8.57 g (0.0357 mole) of the hydrochloride of the above bis(N-benzylglycylmethyl) phosphinic acid in 200 ml of distilled water and hydrogenation is effected at 30°–35° C. After 41% of theory of hydrogen have been taken up, a further 1 g of 5% Pd-C and 200 ml of ethanol are added; after 88% hydrogen uptake, 1 g of Pd-C is again added; after 96% hydrogen uptake, 100 ml of glacial acetic acid are added; and finally after 98% hydrogen uptake, a further 2 g of Pd-C are added. After 4 hours the uptake of hydrogen was 106% of theory and the hydrogenation ceased. The catalyst is then removed by filtration and the filtrate concentrated, affording as residue 0.9 g of a brownish hygroscopic solid which still contains acetic acid. Extraction of the filter cake (catalyst) with water for 12 hours and concentration of the solution affords a further 2 g of orange-coloured end product. The yield of crude product is accordingly 2.9 g (64.5%). Washing with a small amount of water gives a pure white product. For analysis, 1.55 g are dissolved hot in 80 ml of water and crystallised overnight at 4° C.

$C_6H_{13}N_2O_6P$ (240,15)

calculated: C 30,01 H 5,46 N 11,67 P 12,90% found: C 29,68 H 5,65 N 11,58 P 12,84%

The acid can be titrated with tetramethylammonium hydroxide in water as dibasic acid; the third potential drop is weak and cannot be evaluated. The acid is probably in the form of the betain (inner salt).

Solubility in water at 19° C.: 5 g/liter.

31p Chemical shift (in D₂O at pH=3) —17.44 ppm. This is strongly pH-dependent.

IR bands (in KBr): 2.7μ (OH, NH); 8.5μ (P=O); 5.85μ (C=O); 5.3μ (OH).

In a second batch, 6.45 g of the hydrochloride of bis(N-benzylglycylmethyl)-phosphinic acid in 50 ml of water and 200 ml of glacial acetic acid is treated with 1 g of 5% Pd-C and hydrogenated at room temperature. The hydrogen uptake (112% of theory) ceased after 30 minutes.

The catalyst was filtered off and the filtrate, which contained the end product, was concentrated, affording 7.13 g of orange solid. Recrystallisation from water/ethanol yielded 2.66 g (78.5%) of pure bis(glycylmethyl)-phosphinic acid.

Further Derivatives of the formula Ia

Monoamine salts, prepared by concentration of the acid treated with excess amine:

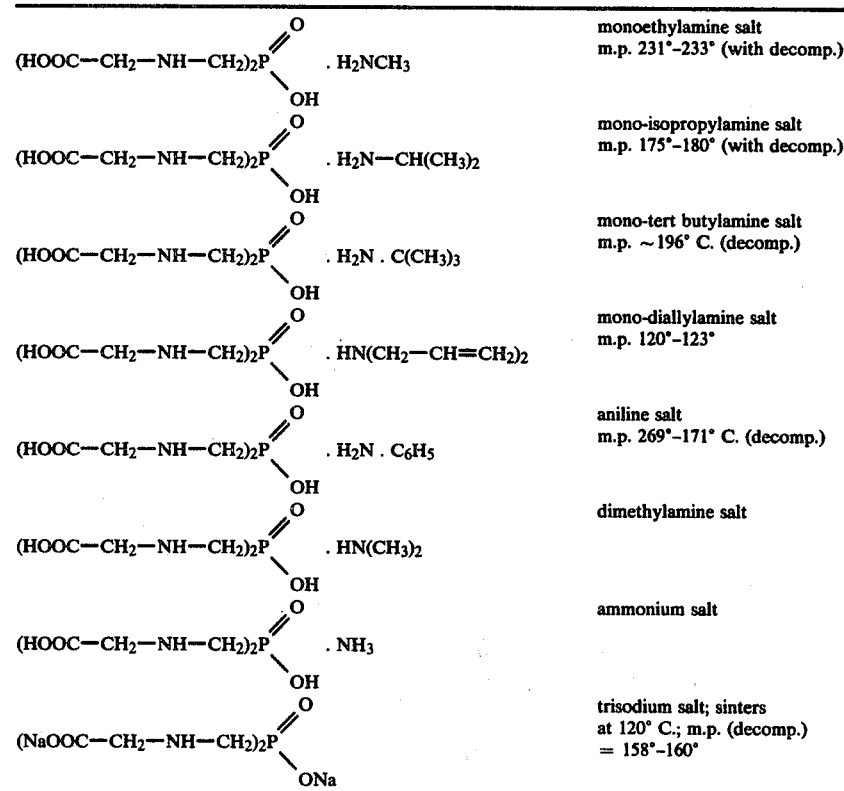

The melting point of the resulting pure bis(glycylmethyl)phosphinic acid

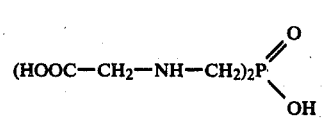

is 270°–282° C. (with decomp.).

Analysis:

Diethyl ester:

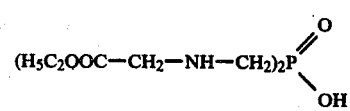

A suspension of 2.4 g of the free acid in 50 ml of ethanol is heated to reflux and then hydrochloric acid gas is slowly introduced, with stirring, over the course of 15 hours. The clear colorless solution is concentrated, affording 3.16 g (91.3%) of diethyl ester, which is obtained as adduct with 1.37 moles of HCl and sinters at 120° C., melts between 133°–140° C., and decomposes above 150° C. The ester hydrochloride is soluble in water, ethanol, methylcellosolve and dimethyl formamide, but is insoluble in acetone.

$C_{10}H_{22}N_2O_6P \cdot 1,37HCl$ (345,96)

calculated: C 34,7 H 6,46 Cl 14,0 N 8,09 P 8,95%
found: C 33,1 H 6,4 Cl 14,0 N 8,2 P 8,9% for inhibiting the growth of grasses, cereals, soya and ornamentals.

The compositions of the present invention can be in the conventional formulations as dusts, tracking powders, granulates, as dispersible concentrates, such as wettable powders, emulsions, emulsifiable concentrates and pastes, as well as solutions, especially in water.

These formulations are prepared with the customary carriers and adjuvants by known methods.

The preferred herbicidal application of the novel

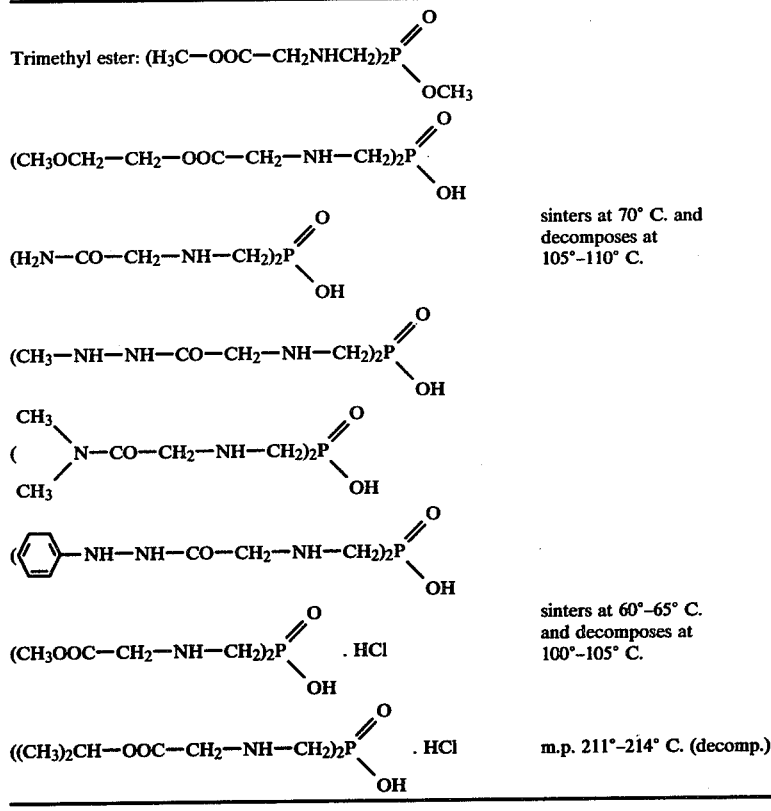

The new derivatives of the formula Ia, both those in which R is hydrogen and those in which R represents a substituent (benzyl etc.), possess herbicidal and plant growth-regulating properies. Both the free bis(glycylmethyl) phosphinic acid and especially alkali metal and amine salts and their esters can be used in particular as contact herbicides and growth inhibitors in post-emergent application.

A number of compounds, for example the hydrochloride of bis(N-benzyl-glycyl-methyl)phosphinic acid also have a fungicidal action, for example against Phytophtora on tomatoes.

In addition to acid addition salts, mention is to be made especially of the alkali metal and alkaline earth metal salts, iron salts etc., the salts of organic amines, protonated and quaternary nitrogen bases, in principle all cations which are tolerated by plant physiology, including those which themselves possess growth inhibiting properties.

The invention also relates to herbicidal and plant growth-regulating compositions which contain a new derivative of the formula Ia as active ingredient, as well as to methods for the total and selective control of weeds in crops of cultivated plants and for inhibiting the growth of mono-and dicotyledonous plants, especially active compounds and compositions is the post-emergent use as contact herbicide.

By the application for inhibiting plant growth, which is also of interest, is meant a control of natural plant development which effects a slowing down of this process. By means of such a method it is possible to bring about artificially retarding phases in the plant development (growth in length, sucker formation, new growth, blossoming, fruit setting etc.). The method of growth regulation is applied at a period of plant development to be determined in each individual case. The new acid and derivatives of the formula Ia and the salts thereof can be applied before or after the emergence of the plants, for example to the seeds or seedlings, to roots, tubers, stems, leaves, blossoms or other parts of plants, for example by applying the active compound itself or in the form of a composition to the plants and/or by treating the nutrient medium of the plant (soil).

The active substances of the present invention thus intervene in the physiological processes of plant growth and are therefore growth regulators which have a growth retarding effect.

The different inhibiting effects depend substantially on the time of application, referred to the development stage of the plant, and on the concentrations employed.

Accordingly, growth inhibitors can also bring about that the nutrients are beneficial to the flower and fruit formation, whereas the vegetative growth is restricted.

The active substances are usually applied in the form of compositions, i.e. after the addition of carriers and other ingredients.

Biological tests in support of the usefulness of the active substances as herbicides and growth inhibitors.

Post-emergent herbicidal action (Contact herbicide)

A large number (at least 7) of weeds and cultivated plants, both mono- and dictoyledonous, were sprayed after emergence in the 4- to 6-leaf stage with an aqueous active substance emulsion in rates of 0.5, 1, 2 and 4 kg of active substance per hectare and kept at 24°–26° C. and 45–60% relative humidity. The test was evaluated 5 and 15 days after treatment in accordance with the following rating:

9=plants undamaged (as untreated control)
1=plants totally withered
8–2=intermediate stages of damage.

Of the tested compounds, the isopropylamine salt and the dimethyl ester of bis(glycylmethyl)phosphinic acid among others exhibited a very pronounced herbicidal action against Setaria, Lolium, Solanum, Sinapis, Stellaria etc.

Growth inhibition in grasses

Seeds of the grasses Lolium perenne, Poa pratensis, Festuca ovina, and Dactylis glomerata were sown in plastic dishes filled with an earth/turf/sand mixture (6:3:1). The emergent grasses were cut back weekly to a height of 4 cm above the soil and 1 day after the last cut were sprayed with aqueous spray mixtures of an active substance of the formula I. The amount of active substance corresponded to a rate of application of 5 kg of active substance per hectare. The growth of the grasses were evaluated 10 and 21 days after application.

Growth inhibition in cereals

Spring wheat (Triticum aestivum), summer barley (Hordeum vulgare) and rye (Secale) was sown in sterilised soil in plastic beakers and reared in a greenhouse. The cereal shoots were treated 5 days after sowing with a spray broth of the active substance. The leaf application corresponded to 6 kg of active substance per hectare. Evaluation is made 21 days later. The isopropylamine salt and the diethyl ester of bis(glycylmethyl)phosphinic acid effect a marked growth inhibition both of grasses and cereal crops.

What is claimed is:

1. Glycylmethylphosphinic acid derivatives of the formula Ia

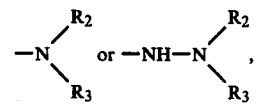

and the salts thereof, wherein
R represents hydrogen, $C_1$–$C_6$ alkyl or mono- to triphenylated methyl,
R' represents —OH or —$OR_1$, wherein $R_1$ represents a cation, substituted or unsubstituted $C_1$–$C_6$alkyl, cycloalkyl, $$-N\begin{array}{c}R_2\\R_3\end{array} \text{ or } -NH-N\begin{array}{c}R_2\\R_3\end{array},$$

in which each of $R_2$ and $R_3$ independently represents hydrogen, lower alkyl or cyanoalkyl, $R_3$ additionally represents phenyl which is unsubstituted or substituted by halogen lower alkyl or nitro, and
R" represents hydrogen, a cation, alkyl, alkenyl, aryl or aralkyl.

2. Glycylmethylphosphinic acid derivatives of the formula Ia of claim 1, wherein R represents a benzyl, diphenylmethyl or triphenylmethyl radical.

3. Bis(glycylmethyl)phosphinic acid of the formula

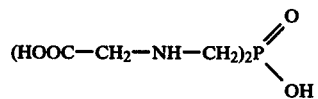

and the salts, esters and amides thereof.

4. A herbicidal and plant growth-regulating composition which contains as active ingredient an effective amount of a glycylmethylphosphinic acid derivative of the formula Ia of claim 1 or a salt thereof, together with a suitable carrier therefor.

5. A method of selectively controlling weeds in post-emergent application which comprises applying thereto a herbicidally effective amount of the active compound of the formula Ia of claim 1.

6. A method of inhibiting the growth of mono- and dicotyledonous plants which comprises applying to the plants or the locus thereof either before or after emergence, a plant growth inhibiting amount of the active compound of the formula Ia of claim 1.

* * * * *